(12) United States Patent
Rezai

(10) Patent No.: US 6,885,888 B2
(45) Date of Patent: Apr. 26, 2005

(54) ELECTRICAL STIMULATION OF THE SYMPATHETIC NERVE CHAIN

(75) Inventor: Ali R. Rezai, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 208 days.

(21) Appl. No.: 10/001,923

(22) Filed: Oct. 23, 2001

(65) Prior Publication Data

US 2002/0116030 A1 Aug. 22, 2002

Related U.S. Application Data

(63) Continuation-in-part of application No. 09/511,841, filed on Feb. 24, 2000, now Pat. No. 6,356,787, and a continuation-in-part of application No. 09/490,617, filed on Jan. 25, 2000, now Pat. No. 6,438,423, and a continuation-in-part of application No. 09/488,999, filed on Jan. 20, 2000, now Pat. No. 6,356,786, and a continuation-in-part of application No. 09/511,839, filed on Feb. 24, 2000, now abandoned.

(51) Int. Cl.[7] .............................................. A61N 1/36
(52) U.S. Cl. .................................... 607/9; 607/17
(58) Field of Search ................... 607/2, 3, 9, 11, 607/14, 17–26

(56) References Cited

U.S. PATENT DOCUMENTS

| | | | |
|---|---|---|---|
| 5,199,428 A | * | 4/1993 | Obel et al. ................ 607/44 |
| 5,578,061 A | | 11/1996 | Stroetmann et al. |
| 5,658,318 A | | 8/1997 | Stroetmann et al. |
| 5,700,282 A | * | 12/1997 | Zabara ......................... 607/9 |
| 6,058,331 A | | 5/2000 | King |
| 6,073,048 A | * | 6/2000 | Kieval et al. ................ 607/17 |
| 6,272,377 B1 | | 8/2001 | Sweeney et al. |
| 6,400,982 B1 | | 6/2002 | Sweeney et al. |
| 2002/0026222 A1 | | 2/2002 | Schauerte et al. |
| 2002/0169365 A1 | | 11/2002 | Nakada et al. |
| 2003/0004549 A1 | | 1/2003 | Hill et al. |
| 2003/0018367 A1 | | 1/2003 | DiLorenzo |
| 2003/0144709 A1 | | 7/2003 | Zabara et al. |
| 2003/0181958 A1 | | 9/2003 | Dobak, III |
| 2003/0181959 A1 | | 9/2003 | Dobak, III |

OTHER PUBLICATIONS

International Search Report for PCT/US02/34000 dated May 8, 2003.

* cited by examiner

Primary Examiner—Jeffrey R. Jastrzab
(74) Attorney, Agent, or Firm—Kenyon & Kenyon

(57) ABSTRACT

The present invention provides a method of affecting physiological disorders by stimulating a specific location along the sympathetic nerve chain. Preferably, the present invention provides a method of affecting a variety of physiological disorders or pathological conditions by placing an electrode adjacent to or in communication with at least one ganglion along the sympathetic nerve chain and stimulating the at least one ganglion until the physiological disorder or pathological condition has been affected.

19 Claims, 5 Drawing Sheets

ELECTRICAL STIMULATION OF THE SYMPATHETIC NERVE CHAIN

This is a CIP of Ser. No. 09/488,999 filed Jan. 20, 2000, now U.S. Pat. No. 6,356,786, and a CIP of Ser. No. 09/490, 617 filed Jan. 25, 2000, now U.S. Pat. No. 6,438,423, and a CIP of Ser. No. 09/511,839 filed Feb. 24, 2000, now abandoned, and a CIP of Ser. No, 09/511,841 filed Feb. 24, 2000, now U.S. Pat. No. 6,356,787.

BACKGROUND OF THE INVENTION

Currently, electrical stimulation of the brain with implanted electrodes is approved for use in the treatment of various movement disorders including Parkinson's and essential tremor. Electrical stimulation is also approved for use in the treatment of tremors in refractory Parkinson's. The principle behind these approaches involves disruption and modulation of hyperactive neuronal circuit transmission at specific sites in the brain. This is achieved by implanting tiny electrodes at these sites to sense aberrant electrical signals and to send electrical pulses to locally disrupt the neuronal transmission.

It has been recognized that electrical stimulation holds significant advantages over alternative methods of treatment. Lesioning tissue destroys all nerve activity and generally causes collateral damage. While there are a variety of different techniques and mechanisms that have been designed to focus lesioning directly onto the target nerve tissue, collateral damage is inevitable. Even when it is possible to direct all lesioning energy onto the target nerve cluster, it is a significant drawback that other functioning of the nerves is lost. In addition, there are several common side effects to lesioning described in the medical literature. It is because of the development of these and other side effects, including the poor response of medical or surgical therapy especially after a delay in treatment, that thoracic or lumbar sympathectomy has not enjoyed a greater popularity among physicians.

SUMMARY OF THE INVENTION

The present invention provides a method of affecting physiological disorders by placing at least one stimulation electrode at a specific location along the sympathetic nerve chain. Preferably, the present invention provides a method of affecting a variety of physiological disorders or pathological conditions by placing an electrode adjacent to or in communication with at least one ganglion along the sympathetic nerve chain.

The method comprises the steps of placing an electrode adjacent to or in communication with at least one ganglion along the sympathetic nerve chain; applying an electric signal to the electrode to stimulate the at least one ganglion; and adjusting at least one parameter of the electric signal until the physiological disorder has been demonstrably affected, modulated, treated, alleviated, arrested, or ameliorated. The at least one ganglion along the sympathetic nerve chain may be any cervical ganglion or ganglia, thoracic ganglion or ganglia, lumbar ganglion or ganglia, or sacral ganglia or any combination thereof associated with a particular physiological disorder to be affected, modulated, treated, alleviated or ameliorated.

The stimulation may be used alone or in combination with chemical or pharmaceutical administration of active agents at the stimulation site or remotely to affect the organ or tissue that is impacted by electrostimulation of the sympathetic nerve chain.

The method of therapeutically treating a physiological disorder over a predetermined time period by means of an implantable pump and a catheter comprising the steps of: implanting at least one electrode having a stimulation portion that lies adjacent a predetermined stimulation site along the sympathetic nerve chain; implanting the catheter that has a discharge portion that lies adjacent a predetermined infusion site along the sympathetic nerve chain; coupling the electrode to a signal generator; operating said signal generator to treat said physiological disorder by stimulating said stimulation site during at least a portion of the predetermined time period; and operating the pump to treat the physiological disorder by discharging a predetermined dosage of at least one drug through the discharge portion of the catheter into the infusion site during at least a portion of the predetermined time period, whereby the physiological disorder is treated.

The aforementioned method may further comprise the steps of: generating a sensor signal related to activity resulting from said physiological disorder; and regulating said steps operating the signal generator and operating the pump in response to the sensor signal. Preferably, a sensor that is implanted into the body generates the signal. Preferably, the regulation step is accomplished by a microprocessor.

A number of treatment regiments utilizing electrical stimulation can be employed for a vast array of physiological disorders or pathological conditions associated with the sympathetic and parasympathetic nervous system. Physiological disorders that may be treated include, but are not limited to, hyperhydrosis, complex regional pain syndrome and other pain syndromes such as headaches, cluster headaches, abnormal cardiac sympathetic output, cardiac contractility, excessive blushing condition, hypertension, renal disease, heart failure, angina, hypertension, and intestinal motility disorders, dry eye or mouth disorders, sexual dysfunction, asthma, liver disorders, pancreas disorders, and heart disorders, pulmonary disorders, gastrointestinal disorders, and biliary disorders. The number of disorders to be treated is limited only by the number, variety, and placement of electrodes (or combinations of multiple electrodes) along the sympathetic nervous system. Furthermore, complications can be minimized to a large extent, or possibly eliminated, by the use of chronic or intermittent electrical stimulation and/or sensing aberrant neuronal signaling continuous or intermittent drug infusion. The reasons are many, and include the possibility of changing which contacts of a multipolar lead are stimulated to minimize stimulating a portion of the ganglion. Adjusting parameters such as frequency or pulse width of the electronic stimulation should also minimize adverse consequences and increase beneficiary effects.

One aspect of the present invention is the stimulation of a sympathetic ganglion or ganglia to treat a disease irrespective of aberrant neuronal signaling. In other words, the methods and devices of the present invention may be used to treat diseases via the sympathetic ganglia, not just disorders associated with or as a result to diseased sympathetic signals.

According to one embodiment of the present invention, a method of affecting heart contractility in a patient comprises placing an electrode in communication with at least one ganglion along the sympathetic nerve chain of the patient wherein the at least one ganglion is associated with heart contractility; applying an electric signal to the electrode to stimulate the at least one ganglion; and adjusting at least one parameter of the electric signal until heart contractility has been affected. Preferably, the at least one ganglion is selected from the group consisting of T-1 through T-4 ganglia, cervical ganglia, and combinations thereof.

Preferably, the application of the electrical signal to stimulate the at least one ganglion is effective in modulating heart contractility. In this embodiment, the patient may have heart failure associated with cardiomyopathy or may have a heart contractility disorder where the heart contractility disorder may be cardiomyopathy or hypertrophic cardiomyopathy.

The method may further comprise administering an amount of a pharmaceutical agent to the at least one ganglion wherein the amount is determined based upon the effectiveness of the electrical stimulation of the at least one ganglion. The administration may be accomplished by a catheter coupled to a pump wherein the catheter is placed in communication with the at least one ganglion along the sympathetic nerve chain of the patient. The method may further comprise sensing a signal related to heart contractility wherein the signal may be an electrical signal or a chemical signal. Preferably, the method further comprises regulating the electrical stimulation in response to the signal.

According to another embodiment of the present invention, a method of affecting coagolapathies in a patient comprises placing an electrode in communication with at least one ganglion along the sympathetic nerve chain of the patient wherein the at least one ganglion is associated with a coagolapathy; applying an electric signal to the electrode to stimulate the at least one ganglion; and adjusting at least one parameter of the electric signal until the coagolapathy has been affected. Preferably, the at least one ganglion is selected from the group consisting of T-1 through T-4 ganglia, cervical ganglia, and combinations thereof.

Preferably, the electrical stimulation is effective in releasing tissue plasminogen activator or angiotensin II.

The method may further comprise administering an amount of a pharmaceutical agent to the at least one ganglion wherein the amount is determined based upon the effectiveness of the electrical stimulation of the at least one ganglion. The administration may be accomplished by a catheter coupled to a pump wherein the catheter is placed in communication with the at least one ganglion along the sympathetic nerve chain of the patient. The method may further comprise sensing a signal related to the coagolapathy wherein the signal may be an electrical signal or a chemical signal. Preferably, the method further comprises regulating the electrical stimulation in response to the signal.

According to another embodiment of the present invention, a method of affecting a bronchial disorder in a patient comprising placing an electrode in communication with at least one ganglion along the sympathetic nerve chain of the patient wherein the at least one ganglion being associated with the bronchial disorder; applying an electric signal to the electrode to stimulate the at least one ganglion; and adjusting at least one parameter of the electric signal until the bronchial disorder has been affected. Preferably, the at least one ganglion is selected from the group consisting of T-1 through T-4 ganglia, cervical ganglia, and combinations thereof.

The method may further comprise administering an amount of a pharmaceutical agent to the at least one ganglion wherein the amount is determined based upon the effectiveness of the electrical stimulation of the at least one ganglion. The administration may be accomplished by a catheter coupled to a pump wherein the catheter is placed in communication with the at least one ganglion along the sympathetic nerve chain of the patient.

The method may further comprise sensing a signal related to the bronchial disorder wherein the signal may be an electrical signal or a chemical signal. Preferably, the method further comprises regulating the electrical stimulation in response to the signal.

The following parameters related to the electrical signal apply to the aforementioned embodiments and embodiments discussed in greater detail herein. The electrical signal to stimulate the at least one predetermined site may be continuous or intermittent. The electrode may be either monopolar, bipolar, or multipolar. Preferably, the oscillating electrical signal is operated at a voltage between about 0.1 $\mu$V to about 20 V. More preferably, the oscillating electrical signal is operated at a voltage between about 1 V to about 15 V. For microstimulation, it is preferable to stimulate within the range of 0.1 $\mu$V to about 1 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the electrode is monopolar; bipolar when the electrode is bipolar; and multipolar when the electrode is multipolar.

DETAILED DESCRIPTION OF THE INVENTION

Figure 1:
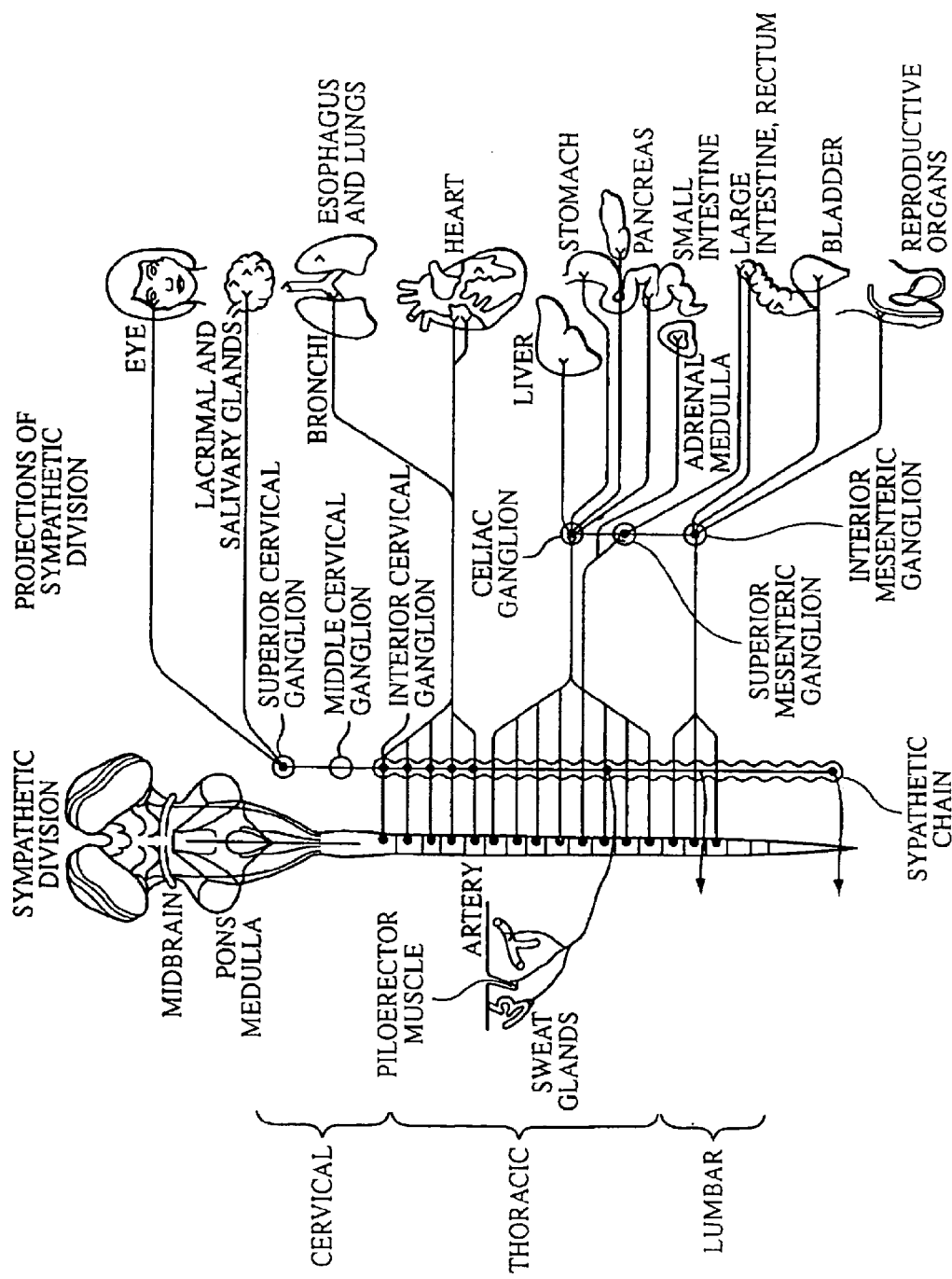
FIG. 1 is a schematic of the Autonomic Nervous System illustrating sympathetic fibers and parasympathetic fibers.

Physiological disorders that may be treated with electrical stimulation are numerous. The cause of many of these physiological disorders may be a dysfunction in anyone or a combination of nerve clusters known as ganglia, a sequence of nerve clusters extending along the outside of the spinal column which form the sympathetic nervous system. Importantly, the present invention also has applicability in treating disorders that are not related to a dysfunction in the ganglia, but rather disorders that may benefit from stimulation of the sympathetic ganglia. For instance, cardiomyopathy as a result of alcoholism may benefit from stimulation of the sympathetic upper ganglia in the thoracic cervical region, but is not a result of aberrant sympathetic nerve clusters.

The sympathetic, along with the parasympathetic, nervous system can also be called the autonomic, or vegetative, nervous system. The autonomic nervous system is comprised of the sympathetic and parasympathetic branches. These two branches in general have opposite functions. Furthermore, the sympathetic and parasympathetic system has a central and a peripheral component. The central component arises from the brain and includes structures such as the frontal cortex, thalamus, hypothalamus, hippocampus, cerebellum and brainstem nuclei including the cranial nerves to name a few. These central components are connected by a vast array of ascending and descending communication tracts, which carry information fasciculi similar to highways of information. The peripheral component of the autonomic nervous system extends from the cranial base to the coccyx, essentially encompassing the entire spinal column. The parasympathetic group lies predominately in the cranial and cervical region, while the sympathetic group lies predominantly in the lower cervical, and thoracolumbar and sacral regions. The sympathetic peripheral nervous system is comprised of the sympathetic ganglia that are ovoid/bulb like structures (bulbs) and the paravertebral sympathetic chain (cord that connects the bulbs). There is also an important distinction between the anatomical structure of the sympathetic chain and the parasympathetic chain. The sympathetic chain is a more tight bundle of nerves that send out long projections. Thus the post-ganglionic fibers are long and go the end organ. Whereas, the parasympathetic nerves are more diffuse network/arrays of ganglia that are very close to the end point and hence the post-ganglionic fibers from them are usually at the end organ. This is an important distinction for neuromodulation therapies since there are multiple discrete ganglia of the sympathetic system that can be affected with wide and far-reaching effects.

The autonomic nervous system has both afferent and efferent components and hence stimulation/modulation can affect both the end organs (efferent) as well as the afferents—to the brain and the central nervous system. This is a similar concept of how the vagus nerve stimulation works, i.e. in a reverse, afferent, or retrograde fashion.

Although sympathetic and parasympathetic fibers (axons) transmit impulses producing different effects, their neurons are morphologically similar. They are smallish, ovoid, multipolar cells with myelinated axons and a variable number of dendrites. All the fibers form synapses in peripheral ganglia, and the unmyelinated axons of the ganglionic neurons convey impulses to the viscera, vessels and other structures innervated. Because of this arrangement, the axons of the autonomic nerve cells in the nuclei of the cranial nerves, in the thoracolumbar lateral comual cells, and in the gray matter of the sacral spinal segments are termed preganglionic sympathetic nerve fibers, while those of the ganglion cells are termed postganglionic sympathetic nerve fibers. These postganglionic sympathetic nerve fibers converge, in small nodes of nerve cells, called ganglia that lie alongside the vertebral bodies in the neck, chest, and abdomen. In particular, the stellate ganglion is located laterally adjacent to the intervertebral space between the seventh cervical and first thoracic vertebrae. The first, second, third and fourth thoracic ganglia lie next to their respective vertebral bodies on either side of the thoracic cavity. The effects of the ganglia as part of the autonomic system are extensive. Their effects range from the control of insulin production, blood pressure, vascular tone heart rate, sweat, body heat, blood glucose levels, sexual arousal, and digestion.

The present invention provides a method of treating physiological disorders by implanting at least one stimulation electrode at a specific location along the sympathetic nerve chain. Preferably, the present invention provides a method of therapeutically treating a variety of physiological disorders or pathological conditions by surgically implanting an electrode adjacent or in communication to a predetermined site along the sympathetic nerve chain on the affected side of the body or, if clinically indicated, bilaterally. FIG. 1 illustrates a schematic of the autonomic nervous system illustrating sympathetic fibers and parasympathetic fibers.

In many instances, the preferred effect is to stimulate or reversibly block nervous tissue. Use of the term "block" or "blockade" in this application means disruption, modulation, and inhibition of nerve impulse transmission. Abnormal regulation can result in an excitation of the pathways or a loss of inhibition of the pathways, with the net result being an increased perception or response. Therapeutic measures can be directed towards either blocking the transmission of signals or stimulating inhibitory feedback. Electrical stimulation permits such stimulation of the target neural structures and, equally importantly, prevents the total destruction of the nervous system. Additionally, electrical stimulation parameters can be adjusted so that benefits are maximized and side effects are minimized.

A variety of approaches are available for upper thoracic implantation of electrodes. Three commonly employed procedures can be adapted for electrode implantation; they are: posterior paravertebral thoracic sympathectomy, thoracoscopic sympathectomy, and retroperitoneal lumbar sympathectomy. Reference is made to "Surgical Management of Pain", Thieme Medical Publishers, Inc. RD 595.5.587 (2001) incorporated in its entirety herein by reference thereto for further details. For open surgery, anterior supraclavicular, transaxillary, and posterior paravertebral approaches are used. Modification of a posterior paravertebral approach is favored by most neurosurgeons. Unlike other approaches, the route does not require separate incisions for bilateral problems. It provides a more direct exposure of the sympathetic ganglia and their rami communicantes. The open surgical options are generally limited for lumbar electrode placement as the retroperitoneal flank approach is predominantly used. Even with improved surgical techniques, open techniques are relatively invasive procedures. The development of video-assisted endoscopic imaging and improved instrumentation during the past decade has let to an increase in endoscopic procedures. The upsurge in the enthusiasm for endoscopic procedures should carry over for lumbar electrode implantation. Percutaneous radiofrequency thoracic implantation technique would appear to offer significant advantages as to the placement of electrodes. It is even less invasive than the endoscopic procedures and an improvement over other percutaneous techniques. This procedure can be done on an outpatient basis with intravenous sedation and local anesthesia; however, it has not gained widespread acceptance because of the high degree of technical difficulty with localization. Real-time intraoperative magnetic resonance imaging (MRI) may be useful in localizing the lumbar sympathetic ganglia.

The present invention avoids a number of the disadvantages previously seen with sympathectomies and the like. The ability to neuromodulate and to detect when and to what degree neuromodulation is necessary is extremely important. The electrode itself may be designed to shield the portion of the electrode not exposed to the ganglia. Also, the electrode may be fixed to the bone, soft tissue, ribs, or vertebra body. All that is required is that the electrode be exposed or in contact with the desired ganglia of the sympathetic nerve chain.

Preferably collateral stimulation of the muscle is avoided while so avoiding compression of the ganglia to avoid nerve death. The innervation of the sympathetic nerve chain provides ample opportunity to utilize the methods and devices of the present invention. The electrode itself may be implanted within the ganglia.

Figure 2:
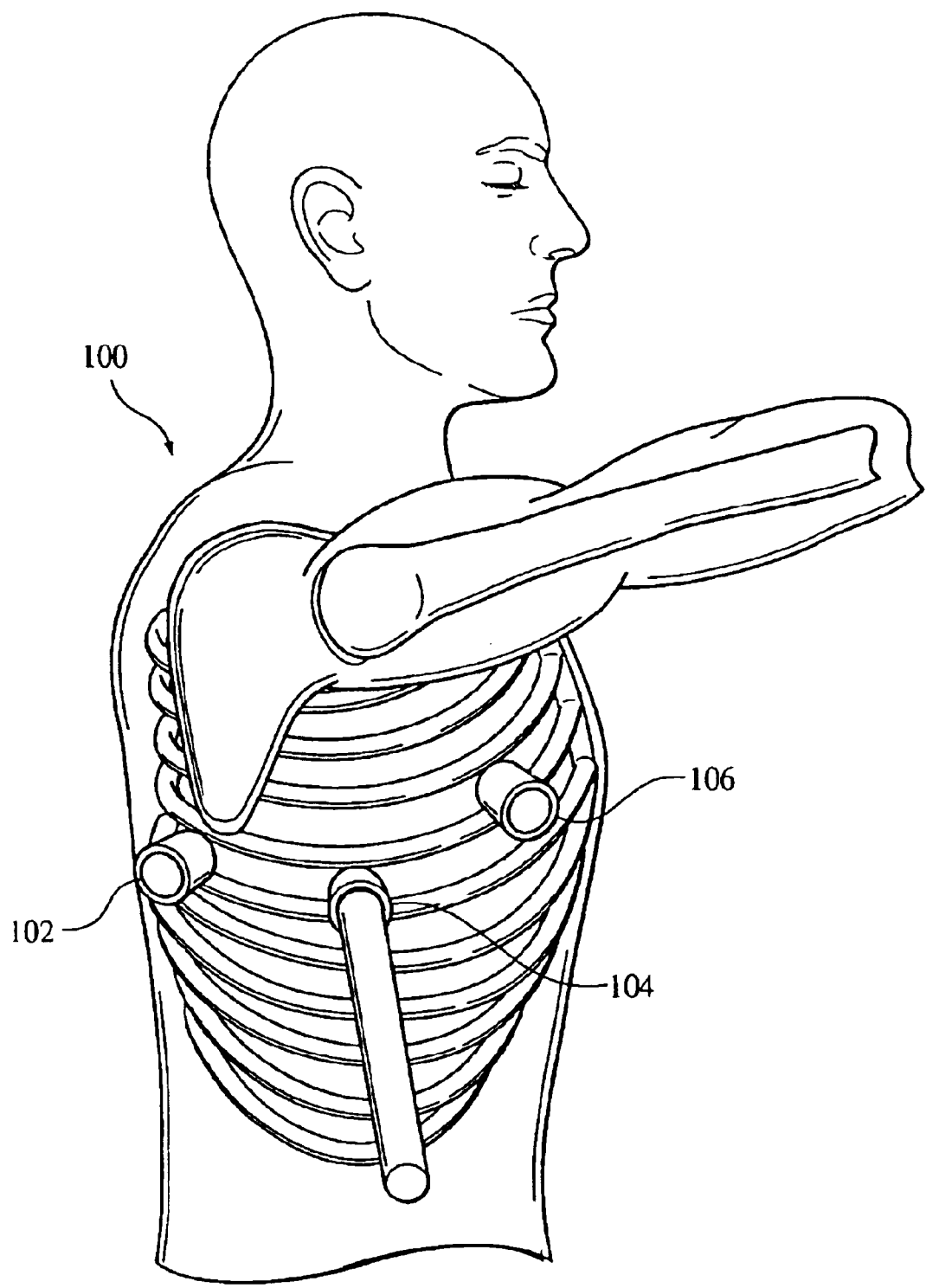
FIG. 2 is a schematic illustration of a patient lying in the lateral decubitus position having one visualization port in the fifth intercostal space at the mid-axillary line and two instrument ports at the fourth and fifth intercostal space at the anterior and posterior axillary lines, respectively.

Referring now to FIG. 2, a patient 100 is illustrated in the decubitus position where the hips of the patient 100 are preferably below the flexion joint of the operating room table. Subsequent flexion of the table allows some separation of the ribs by dropping the patient's hips and therefore increasing the intercostal space to work through. The ipsilateral arm is abducted on an arm holder. Rotating the table somewhat anteriorly and using reverse Trendelenburg positioning further maximizes the exposure to the superior paravertebral area by allowing the soon to be deflated lung (see FIGS. 3 and 4) to fall away from the apical posterior chest wall. This is the preferred position of the patient 100 prior to performing the procedure as this position exposes the vertebral bodies where the sympathetic nerve chain lies extrapleurally.

The procedure begins with placing the patient 100 under general anesthesia and intubated via a double lumen endotracheal tube. The double lumen endotracheal tube permits ventilation of one lung and collapsement of the other lung that is to be operated upon without using carbon dioxide insufflation. One incision is made in the midaxillary line in the fifth intercostal space that is identified as port 104. Port 104 can be used for various reasons, but it is preferred that port 104 is used as a telescopic video port which will provide video assistance during the procedure. While under endoscopic observation, a second incision is made in the third or fourth intercostal space at the anterior axillary line that is identified as port 106. Port 106 is preferably used as an instrument channel. A third incision is made at the posterior axillary line just below the scapular tip in the fifth interspace that is identified as port 102. Port 106 is preferably used as a second instrument channel. Preferably, the three incisions made during the thoracoscopic sympathectomy are approximately 2 cm in length. Additional incisions (i.e., ports) can be made as necessary.

Figure 3:
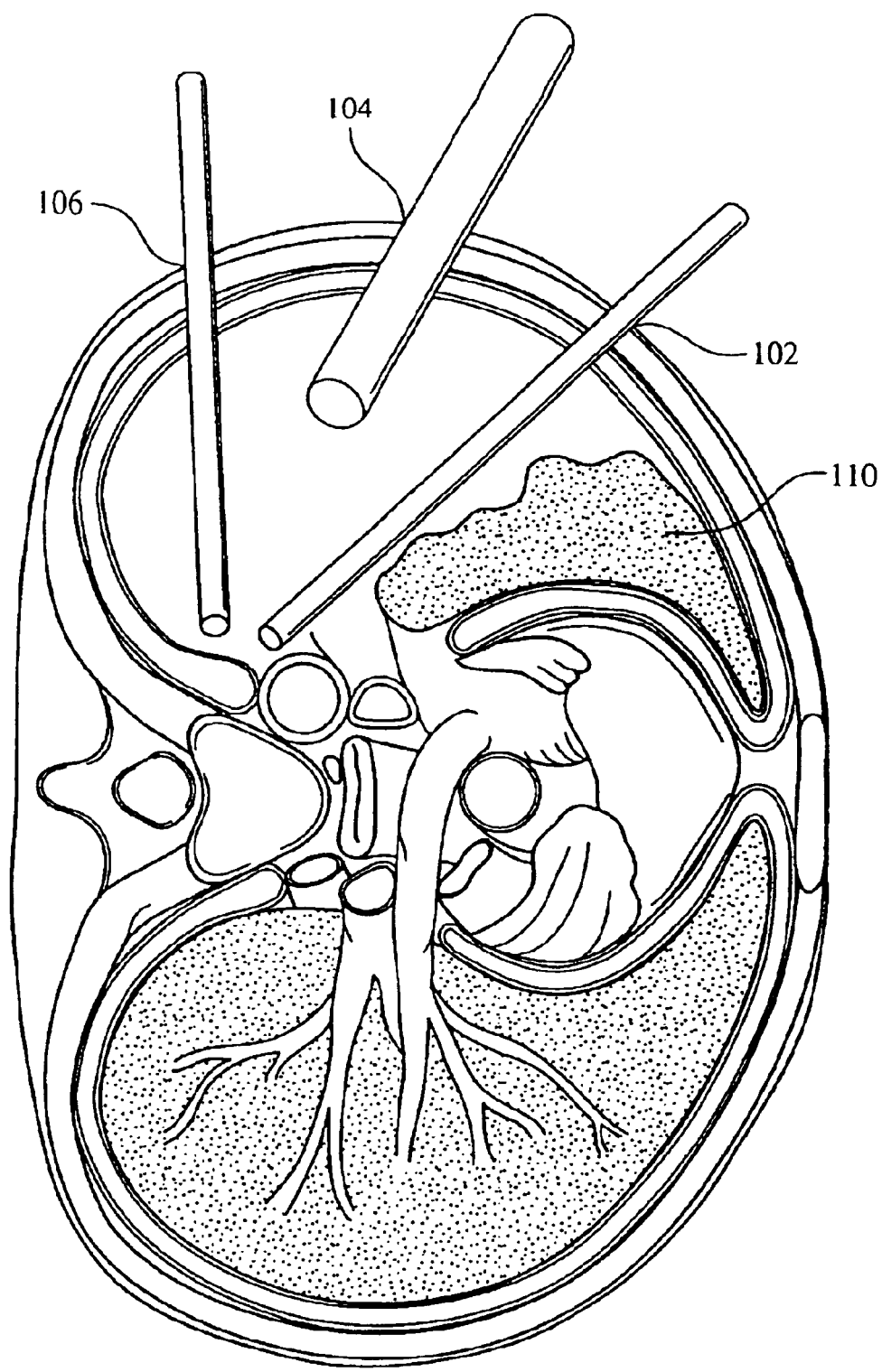
FIG. 3 is an axial cross section view of the upper thoracic region including one visualization port and two instrument ports wherein the two instrument ports have disposed therethrough endoscopic instruments accessing the ipsilateral paravertebral region where the sympathetic nerve chain lies.
Figure 4:
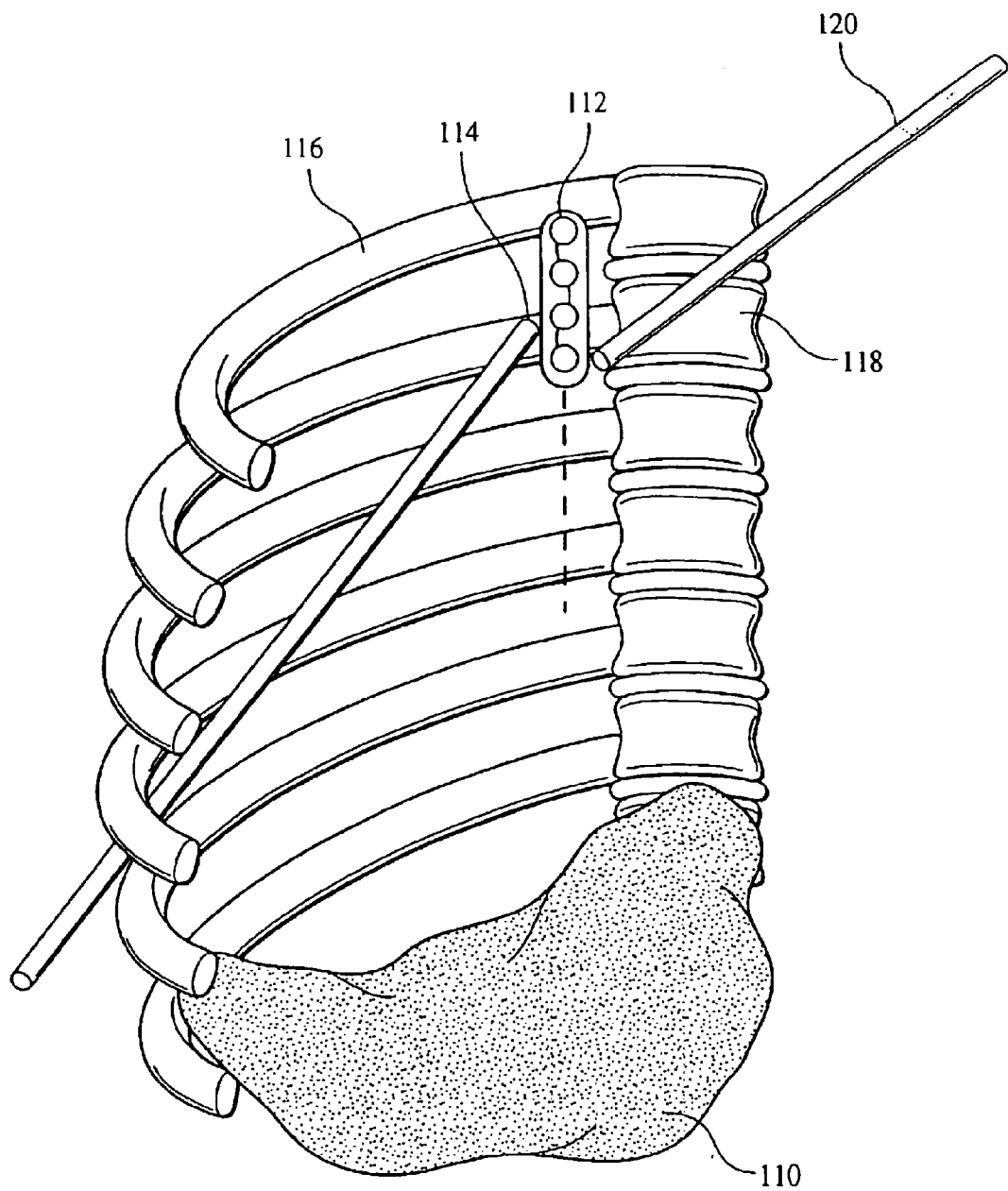
FIG. 4 is an exposed view of the left hemithorax displaying one instrument tenting the parietal pleura while the second endoscopic instrument is incising the parietal pleura to expose the sympathetic nerve chain.

Referring now also to FIGS. 3 and 4, in which axial cross section and exposed views of the surgical signal are provided, respectively, the surgical exposure and preparation of the relevant portion of the sympathetic nerve chain for the treatment of various physiological and pathological conditions is described. After the lung 110 is collapsed, and if necessary, retracted down by a fanning instrument via one of the working ports, the sympathetic nerve chain 112 is visualized under the parietal pleura 114 as a raised longitudinal structure located at the junction of the ribs 116 and the vertebral bodies 118. The parietal pleura 114 is grasped between the first and second ribs in the region overlying the sympathetic nerve chain 112 and scissors 120 or an endoscopic cautery is used to incise the parietal pleura 114 in a vertical manner just below the first rib thereby exposing the sympathetic nerve chain 112.

Figure 5:
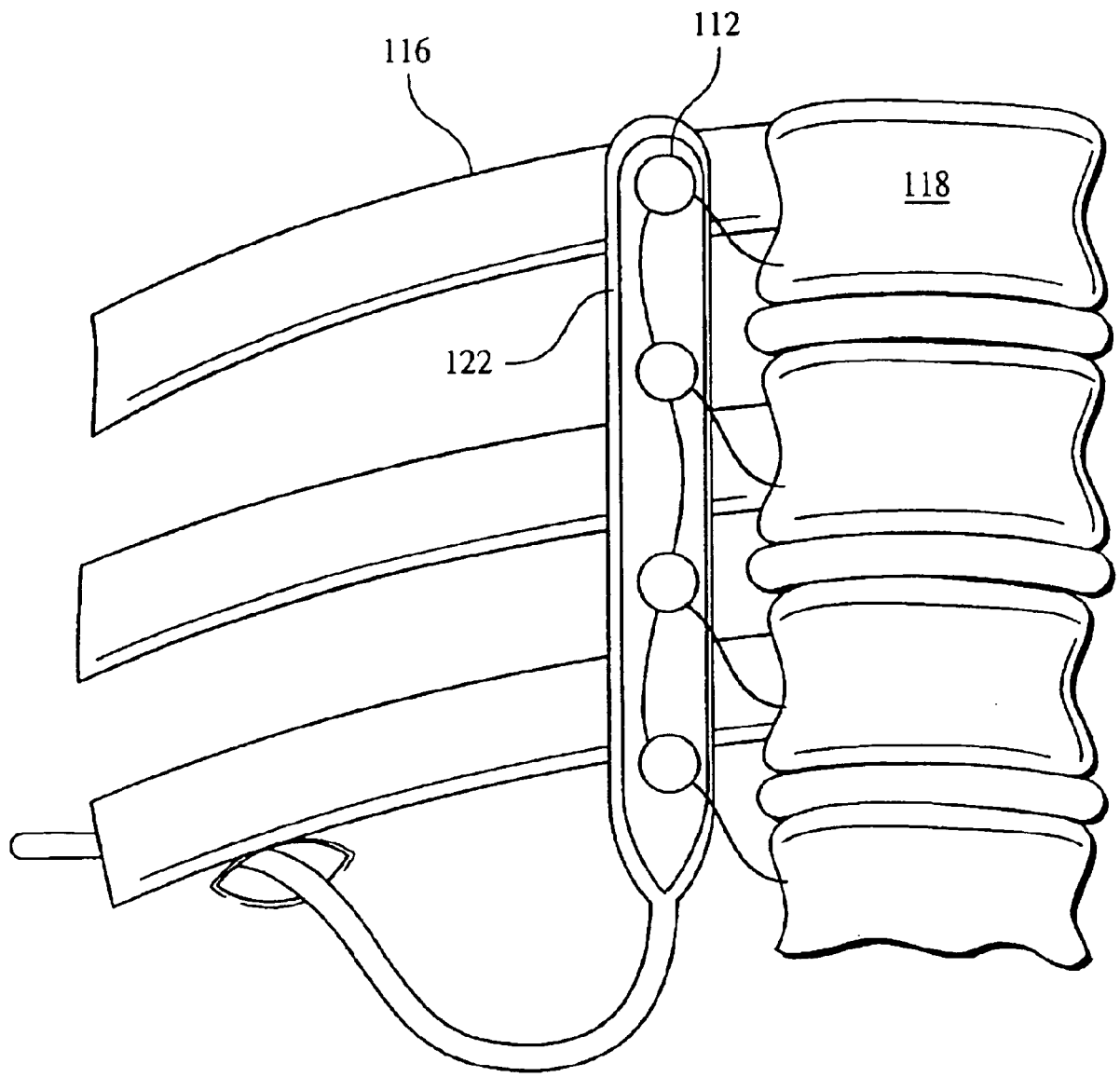
FIG. 5 is a side view of an exposed superior thoracic ganglia in which an electrical stimulation electrode is disposed adjacent thereto.

Referring now also to FIG. 5, in which the implantation of a multichannel stimulation electrode 122 at a specific location of the sympathetic nerve chain is shown, the implantation of the stimulation electrode 122 is now described. Once the sympathetic nerve chain 112 has been exposed, a multichannel stimulation electrode 122 is implanted adjacent to a predetermined site along the sympathetic nerve chain that is associated with the physiological disorder or pathological condition being treated. Preferably, predetermined site along the sympathetic nerve chain, which is associated to the physiological disorder or pathological condition being treated, is directly into or adjacent to any single ganglion along the sympathetic nerve chain or any combination of ganglia along the sympathetic nerve chain. The stimulation electrode 122 is preferably sutured in place to the nearby tissue or parietal pleura 114. The vicinity of the sympathetic nerve chain for which the stimulation electrode is positioned depends on the physiological disorder or pathological condition being treated.

The electrode 122 is connected to a power source (most likely a battery/pulse generator) which provides the energy/power source for the stimulation. The power source could be a battery implanted on or adjacent to the electrode 122 or it could be implanted at a remote site on the head or thorax away from the site of stimulation (as in cardiac pacemakers or deep brain stimulators). The connection cable can be passed out of the thoracic cavity via one of the neighboring surgical ports, and tunneled subcutaneously to the electrical signal source which, in turn, is operated to stimulate the predetermined treatment site over the sympathetic ganglia, such that the clinical effects of the physiological disorder are reduced with minimal side effects.

Once the electrode 122 is secured in place, the electrical signal source is activated thereby applying an oscillating electrical signal, having a specified pulse width, to the electrode 122. The electrode 122 may be implanted, sutured, stapled, or otherwise secured in place. The electrode 122 is preferably in contact with the ganglia, but may be simply in electrical communication. The oscillating electrical signal may be applied continuously or intermittently. Furthermore, if an electrode is implanted directly into or adjacent to more than one ganglion, the oscillating electrical signal may be applied to one electrode and not the other and vice versa. One can adjust the stimulating poles, the pulse width, the amplitude, as well as the frequency of stimulation to achieve a desired goal. The application of the oscillating electrical signal stimulates the area of the sympathetic nerve chain where the electrode 122 was placed. This stimulation may either increase or decrease nerve activity. The frequency of this oscillating electrical signal is then adjusted until the physiological disorder being treated has been demonstrably alleviated. This is then considered the ideal frequency. Once the ideal frequency has been determined, the oscillating electrical signal is maintained at this ideal frequency. Preferably, the oscillating electrical signal is operated at a voltage between about 0.1 $\mu$V to about 20 V. More preferably, the oscillating electrical signal is operated at a voltage between about 1 V to about 15 V. For microstimulation, it is preferable to stimulate within the range of 0.1 $\mu$V to about 1 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the electrode is monopolar, bipolar when the electrode is bipolar, and multipolar when the electrode is multipolar.

The electrodes or their casing may be made of inert material (silicon, metal or plastic) to reduce the risk (chance) of triggering an immune response. Electrodes should be studied for suitability to MRI and other scanning techniques. The electrodes should be anchored securely at the site of implantation. The stimulating signal may have variable parameters including voltage, frequency, current, intensity, and pole combinations. These parameters can be modulated by setting and adjusting the stimulus. The electrode signal (output) can be adjusted to specified settings based on the degree of relief at the time of surgical implantation or later on following onset of acute episodes. The direction of current flow may need to be and is preferably reversible. The stimulating signal itself may be intermittent or continuous depending on the setting.

The setting of the electrodes can be adjusted externally using currently available technology utilizing magnetic signals conventional telemetry. As the technology progresses, other modalities may be used to adjust and modulate the parameters of the stimulating electrodes. The electrode would then be connected to the remotely placed battery via wires.

The choice of electrodes for stimulation influences how much current is required to produce depolarization. When the stimulating electrode is the cathode (negative), it causes the current to flow from the cathode to the anode (positive) along the nerve towards the electrode and causes depolarization of the neural tissue (neurons, axons) at a much lower current than when the stimulating electrode is the anode (positive).

The electrical discharge cycle (action potential) of a typical neuron may last up to 1 millisecond and the internal voltage of the neuron may change from −70 to +20 millivolts. Peripheral nerve stimulation can be done by the transcutanous method where the stimulating electrodes are placed on the skin overlying the nerve. Another mode of peripheral nerve stimulation involves placing a stimulating needle electrode through the dermis adjacent and occasionally directly on the nerve. The stimulating parameters are a function of the distance of the stimulating electrode from the nerve.

Electrical stimulation of the sympathetic ganglia can have a heretofore unexpected beneficial impact on the body, particularly regarding organs or systems associated with the ganglia being stimulated. Stimulation of the ganglia may result in functional activation or inhibition of the system associated with the particular sympathetic ganglia and nerve. These functions include affecting (increasing or decreasing) the movement of organs, the secretion of hormones or enzymes, or affecting certain functions associated with the organ and controlled to some degree by the sympathetic ganglia.

The following Examples break the ganglia down into region, organ or system, and diseases that may benefit from electrical stimulation. The three basic areas of ganglia location for purposes of the present invention are cervical ganglia, thoracic ganglia, and lumbar ganglia. The sacral region may also be a region of electrode implantation, but, technically, there are no sympathetic ganglia in the sacral region. However, nerves from other regions (e.g., lumbar) that are in communication external to this region and may be stimulus as a means to stimulate the lumbar ganglia. Obviously, these can be further subdivided into upper, mid, and lower regions respectively. Placement of electrodes in these regions or portions of these regions appear to have a desirable impact on many diseases associated with the human anatomy. Although not an indication of priority of disease, the following examples are provided to illustrate the utility and novelty of the present invention to illustrate the utility of the present invention and are not meant to be limiting. For purposes of brevity, a specific ganglion will be represented by a letter and number combination or series of letter and number combinations (e.g., the second thoracic ganglion will be represented as "the T-2 ganglion" and the fourth lumbar ganglion will be represented as "the L-4 ganglion", etc.).

EXAMPLE 1

Sympathetic electrical stimulation may be used, for example, to treat cardiac disorders for which the sympathetic output is abnormally high or low. The sympathetic pre-ganglionic fibers lay mainly in the sympathetic trunk ganglia from the superior cervical to the T-4 or T-5 ganglia and then the post-ganglionic fibers, which are longer, go to the heart directly via the long cervical and thoracic sympathetic cardiac nerves. In fact, stimulation of the spinal cord relieving and increasing microcirculation of the heart may indeed be mediated through the spinal cord fibers which are sympathetic and which are going through highways/tracts in the spinal cord on their way from the central autonomic nervous system to the sympathetic ganglia. In contrast, the parasympathetic pre-ganglionic fibers to the heart reach the heart via the cardiac branches of the vagus nerve and relay in the ganglia of the cardiac plexus on in small subendothelial ganglia which are in or surrounding the heart. For the purposes of providing details in the discussion to follow, three representative examples will be stressed: heart failure, arrythmia, and angina pectoris. The most prevalent cause of death in developed countries is cardiac related. These cardiac abnormalities can vary from valvular disease to vascular disease to electrical irregularities. The current mainstay of treatment for many of these disorders involves a vast array of medications, surgical approaches, as well as endovascular methodologies. The most commonly employed general treatment involves the use of medications. While many drugs have been found to alleviate cardiac-related symptoms, very few have actually been demonstrated to prolong life after a myocardial infarction. The two most commonly cited drugs with life-prolonging properties are acetyl salicylic acid (aspirin) and beta-blockers. Beta-blockers reduce the effects of the sympathetic system on the heart via a variety of different mechanisms, including blood pressure reduction, decreased heart rate, decreased cardiac contractility, and thus, decreased cardiac oxygen demand. Perhaps the most beneficial effect of beta blockade, in terms of increasing survival in patients with cardiac disease, is its anti-arrhythmic effect. These effects prolong and enhance cardiac functionality and efficiency. Their mode of action involves the chemical blockade of the sympathetic efferent nerve fibers that terminate on the heart. These nerve fibers originate in a nerve cluster known as the stellate ganglia. Beta-blockers act by blocking the beta-adrenergic system, either non-selectively, or specifically the beta-1 receptors which are almost exclusively found in the heart. The non-selective beta-adrenergic blockers, such as propranolol, also block the beta-2 system, which in susceptible individuals can cause life-threatening bronchospasm. As medications are administered systemically, even the specific beta-1 blockers have known side-effects including lethargy, hallucinations, nausea, diarrhea, impotence, hypoglycemia without the normally accompanying tachycardia, fever, and arthralgia. Accordingly, it would appear that for any disease or condition for which beta-blockers are useful, the electro-stimulation of the present invention would have application. An additive, or even synergistic, effect may be seen with both beta-blockers and electrostimulate. Electrostimulation may reduce side effects and/or efficiency of beta-blockers.

The sympathetic outflow to the heart originates in the stellate and the first four thoracic ganglia. The sympathetic nervous system sends signals to the heart, increasing cardiac contractility, heart rate, and prolonging the QT-interval. In particular, the stellate ganglion, as well as the first, second, third and fourth thoracic ganglia lie next to their respective vertebral bodies on either side of the thoracic cavity. The left side, however, has been demonstrated to provide the majority of the sympathetic output to the heart. Minimal changes in cardiac parameters are seen when stimulating or lesioning the right side. In fact, left side stellate ganglion stimulation in humans has been demonstrated to effect the ejection fraction of the heart, the QT interval, and blood pressure.

Stimulation of the sympathetic ganglion (stellate and cervical) in dogs has been shown to modulate the levels of angiotensin II. Accordingly, stimulation of the sympathetic ganglion may benefit the angiotensin system. Angiotensin II is a compound (octapeptide) that is involved in pathophysiology of multiple cardiac, vascular and renal diseases. Angiotensin II is known to influence cardiac function and has been shown to effect coronary artery smooth muscle cells, endothelium and sympathetic nerve endings. Aberrant functioning of the Renin-angiotensin system has also been implicated in hypertension and renal disorders. A variety of pharmacological therapies are aimed at blocking the production and/or the receptors for angiotensin II. The involvement of the local angiotensin system in ganglionic functions was discussed in the article "Upregulation of Immunoreactive Angiotensin II Release and Angiotensinogen mRNA Expression by High Frequency Preganglionic Stimulation at the Canine Cardiac Sympathetic Ganglia" by Kushiku et al. published in Circulation Research, Pgs. 110–116, Jan. 5/19, 2001 which is hereby incorporated by reference in its entirety.

Also, sympathetic stimulation may also benefit hypercoagulation, prothrombotic states. Sympathetic neurons synthesize, transport and store tissue plasminogen activator (TPA) at the axonal terminals that innervate the vessel wall. Sympathetic stimulation induces a surge of TPA from the vessel wall into the blood. TPA is a protein that has anti-thrombotic/clotting effects (i.e., it essentially dissolves microclots). Sympathetic ganglionic stimulation may be helpful in patients with systemic clotting problems.

Regarding the treatment of abnormal cardiac sympathetic output (e.g., angina pectoris or heart failure), the stimulation electrode 122 is implanted over the inferior third of the stellate ganglion. Preferably, the stimulation electrode 122 is implanted over the inferior third of the stellate ganglion and over the upper thoracic ganglia. More preferably, the electrode 122 is implanted over the inferior third of the stellate ganglion and over the T-1, T-2, T-3 and T-4 ganglia. For example, for a patient with angina pectoris who is post-myocardial infarction, one wishes to decrease heart rate and oxygen consumption, as well as increase heart rate variability, all of which have been demonstrated to have a positive prognostic outcome. By stimulating at a high frequency, the sympathetic outflow would be inhibited. In a patient with cardiac failure on the other hand, stimulating at a low frequency would drive sympathetic flow and would increase cardiac contractility and cardiac output. Adjusting the frequency, in particular, can either drive (increase) or inhibit sympathetic output to the heart to achieve desired effects. Thus, the thoracic ganglia may support not only vasodilatory or vasoconstrictive effects of the vascular system, but also the contractility of the heart. Implantation of the electrode 122 over the lower thoracic ganglia may also affect hormonal release for hypertension.

EXAMPLE 2

Complex regional pain syndrome (CRPS) type 1, commonly known as reflex sympathetic dystrophy syndrome, or RSDS, was described 25 years ago. Several synonyms have been commonly employed in describing parts or all of this syndrome, including Raynaud's syndrome, vasomotor instability, occupational digital thrombosis, arteriosclerotic obliterative disease, etc. CPRS Type II, on the other hand, also known as causalgia, is a regional pain syndrome that develops after injury to a peripheral nerve, as first described during the Civil War by Dr. W. Mitchell. Spontaneous pain develops in the territory of the affected nerve that may then spread beyond that region. Vasomotor abnormalities and focal edema may occur alone or in combination in both CRPS types I and II. These are a severely disabling group of illness with simultaneous involvement of nerve, skin, muscle, blood vessels, and bones. While there are many symptoms associated with CRPS, the only common denominator is pain. The pain usually appears in one or more extremities, and is described as chronic, burning and constant in nature. A syndrome of total body pain due to CRPS has been described as well. The remainder of symptoms may or may not occur. These symptoms include swelling, limited motor function which may lead to atrophy or dystrophy, tremor focal dystonia or spasm, skin changes such as atrophy, dryness, and scaling, as well as bony changes with joint tenderness and swelling. In addition, vasomotor instability consisting of Raynaud's phenomenon (e.g. color changes and pain in fingers when exposed to cold), vasoconstriction or dilatation leading to cold and warm extremities respectively, as well as increased sweating.

The cause of the condition is currently not well understood and is often unrecognized. A number of precipitating factors have been associated with CRPS including minor trauma, cerebral or spinal cord lesions, ischemic heart disease and/or myocardial infarction, and repetitive cumulative trauma, such as carpal tunnel syndrome. However, in many of the patients a definite precipitating event can not be identified. Duration of CRPS varies, in many cases the pain continues on for at least two years and in some cases, indefinitely. Some patients experience periods of remissions and exacerbations. Periods of remission may last for weeks, months or years. The mean age of onset is in the mid-thirties and there is increasing evidence that the incidence of CRPS in adolescents and young adults is on the rise. In Germany alone, for example, the annual incidence of RSD is estimated at 15,000. Both sexes are affected, but the incidence of the syndrome is higher in women. Nonsurgical treatment consists of medicinal therapy, physical therapy, various peripheral or sympathetic nerve blocks, transcutaneous electrical nerve stimulation, or surgical sympathectomy. Patient response to therapy directly correlates to early diagnosis and treatment. However, the overall response rate to treatment is poor with over 50% of patients having significant pain and/or disability years later.

Regarding the treatment of complex regional pain syndrome Type I (specifically upper extremity reflex sympathetic dystrophy), the stimulation electrode 122 is implanted over the inferior portion of the stellate ganglion. Preferably, the stimulation electrode 122 is implanted over the inferior portion of the stellate ganglion and over the upper thoracic ganglia. More preferably, the stimulation electrode 122 is implanted over the inferior third of the stellate ganglion and over the T-2, T-3, and T-4 ganglia.

EXAMPLE 3

Hyperhydrosis is characterized by excessive sweating. The disorder can be quite pronounced, and it affects hundreds of thousands of patients, many of who are not simply embarrassed by the condition, but are in fact truly handicapped. These handicaps include constant wiping of hands, social avoidance, work avoidance, and difficulty performing tasks such as holding a steering wheel while driving. It has been estimated that 0.1–0.2% of young adults suffer from severe palmar hyperhydrosis.

In patients suffering from palmar or other forms of hyperhydrosis, the first, second, third and fourth thoracic ganglia play a major role in the abnormal signal generation to the sweat glands of the hand. Presently, there is no effective medicinal treatment for the condition. The present standard of care for the interventional treatment of palmar hyperhydrosis is the lesioning of the stellate and upper thoracic ganglia via one of several surgical approaches.

Regarding the treatment of palmar or axillary hyperhydrosis, the electrode 122 is implanted over the inferior portion of the stellate ganglion. Preferably, the stimulation electrode 122 is implanted over the inferior third of the stellate ganglion and over the upper thoracic ganglia. More preferably, the stimulation electrode 122 is implanted over the inferior portion of the stellate ganglion and over the T-2, T-3, and T-4 ganglia.

EXAMPLE 4

Facial blushing is excessive and frequent redness of the face that is easily elicited by emotional or social stimuli. The instantaneous appearance of blushing is produced by normal events in daily life such as eating with other people, meeting someone, shopping, speaking in public, and so on. The disorder can be quite pronounced, and it effects a significant percentage of people who suffer from social phobia. The prevalence rate of social phobia is approximately 10%, or 30 million people in the United States alone. While many in the medical community consider facial blushing trivial or normal, many patients, in fact, state that it causes a significant negative impact on their quality of life. In a recent study of 244 patients undergoing ablative surgery for this disorder, 17% of patients were forced to take periodic sick leave or early retirement. Suicide was considered among a quarter of patients, while half of patients used alcohol as a means of relieving their facial blushing.

Normal blushing of skin, and in particular, the face, is a reflection of the vasodilatory effects of blood vessels in the skin caused by emotional stimuli. This effect is mediated by the sympathetic nervous system originating in the upper thoracic portion of the sympathetic chain. In patients suffering from facial blushing, the first, second, and third thoracic ganglia play a major role in the abnormal signal generation to the blood vessels of the face and neck. Presently, there is no effective medicinal treatment for the condition. In the aforementioned study, 22% of patients had tried medications called beta-blockers with minimal or no relief. Many patients also undergo expensive psychological treatments, such as cognitive and behavioral therapies, without significant relief of symptoms. The present standard of care for the interventional treatment of facial blushing is the lesioning of the stellate and upper thoracic ganglia via one of several surgical approaches.

Regarding the treatment of facial blushing, the stimulation electrode 122 is implanted over the inferior portion of the stellate ganglion. Preferably, the stimulation electrode 122 is implanted over the inferior third of the stellate ganglion and over the upper thoracic ganglia. More preferably, the stimulation electrode 122 is implanted over the inferior portion of the stellate ganglion and over the T-1, T-2, and T-3 ganglia.

EXAMPLE 5

Stimulation of the T-6 through T-12 ganglia as well as the lumbar sympathetic ganglia innervates the intestines and may be helpful in treating gastrointestinal motility disorders. Also, electrical stimulation of the thoracic sympathetic ganglia may be helpful in treating GI, bowel, and visceral pain as well as that of hepatic and biliary pain. Furthermore, stimulation of the lumbar sympathetic ganglia and sacral sympathetic nerves may be helpful in treating pelvic pain (colon, interstitial cystitis, bladder, ovaries and other reproductive organs) and pain of the lower extremities including RSD/CRPS. Additionally, electrical stimulation of the lower thoracic and lumbar sympathetic ganglia and sacral sympathetic nerves may be helpful in treating bladder dysfunction and other bladder conditions.

Regarding the above disorders and conditions, the stimulation electrode 122 is implanted in the lower thoracic and lumbar ganglia. Implantation of the electrode and subsequent stimulation of electrode 122 of the lower thoracic and lumbar ganglia can affect the gastrointestinal system to increase or decrease motility of the system with application to permit intestinal gastric gallbladder, liver, and pancreatic rest in states of inflammation including cholecystitis, pancreatitis, inflammatory bowel disease and constipation. Accordingly, implantation of the electrode on the T-9, T-10, and T-11 ganglia as well as potentially with L-1, L-2, and L-3 ganglia could affect motility of the gastrointestinal system.

EXAMPLE 6

Stimulation of the lower cervical and upper thoracic sympathetic ganglia may impact the tracheal, bronchial, and pulmonary systems. Therefore, electrical stimulation of the lower cervical and upper thoracic sympathetic ganglia may be helpful in treating bronchospasm episodes or chronic spasms of the airways (asthma and other entities) by controlling the contraction of the smooth muscles of the airways.

Accordingly, in this example, implantation of the electrode 122 over the inferior portion of the T-1 through T-5 ganglia could be a very useful application of the present invention to treat asthma. Also, implantation of the electrode 122 over the inferior cervical ganglion could also be useful to treat asthma.

EXAMPLE 7

Implantation of the electrode 122 over the lower thoracic and lumbar regions may also impact renal disease or other kidney diseases.

Regarding the treatment of real disease, the electrode 122 is implanted over any one or combination of lower thoracic ganglia. Preferably, the stimulation electrode 122 is implanted over the T-5 ganglion through T-12 ganglion.

EXAMPLE 8

Stimulation of the lower thoracic and lumbar ganglia may be helpful in treating sexual dysfunction including impotence and other conditions. Implantation of electrode 122 over the lower lumbar region may impact sexual dysfunction due to the association of the sympathetic nerve with the testicles and penis.

Regarding the treatment of sexual dysfunction or other conditions, the electrode 122 is implanted over any one or combination of lumbar ganglia. Preferably, the stimulation electrode 122 is implanted over the L-1 through L-3 ganglia.

EXAMPLE 9

The T-6 through T-12 ganglia may be stimulated for innervation of the pancreas and potential modification of the pancreatic enzymes and hormones such as insulin and glucagon, lipase and others needed for metabolism. Implantation of the electrode 122 as positioned above the lumbar region may affect the pancreas. This would affect hormonal release for diabetes.

Regarding the treatment of pancreas or liver disorders, the electrode 122 is implanted over any one or combination of the lower thoracic ganglia. Preferably, the stimulation electrode 122 is implanted over the T-5 through T-12.

The aforementioned procedures can most easily be accomplished by using existing electrode configurations or modifications thereof, with the distal end being more superior, and the proximal end and the connection cable being more inferior. For disorders requiring stimulation of the thoracic ganglia, the electrode 122 can be inserted into the thoracic cavity and held in place via the posterior axillary line incision and sutured by using the other working port. The connecting cable can be left at the posterior axillary line port after the lead has been secured with some remaining "slack" of connecting cable being left in the inter-pleural space. The proximal end of the connecting cable/tube can be brought out of the thoracic cavity, and via an extension cable/tube, be tunneled subcutaneously and connected to an electrical pulse generator or infusing pump. The pulse generator or pump may be placed in the subcutaneous tissues of the flank area, abdominal wall area, or buttock area, etc. Any excess fluid is suctioned from the thoracic cavity and the lung is reinflated. A suctioning chest tube may or may not be used depending on the presence or absence of damage to the visceral pleura of the lung. The incisions are closed, and a chest x-ray is obtained in the recovery room to ensure the lung has reinflated. Electrical stimulation or drug infusion therapy may be started immediately, or after a delay, allowing for some healing to occur first.

Alternatively, one may prefer not to incise the parietal pleura 114 if electrical stimulation is used, as the current generated may modulate the functioning of the ganglia through the pleural surface. Pending the preference and comfort level of the surgeon, various test procedures may be employed to maximize the probability of future effective therapy.

Alternatively, another embodiment includes a catheter with either end- or side-apertures placed over the ganglia of interest and is connected in a similar fashion to an infusion pump device. An infusion pump device in accordance with this embodiment may be implanted below the skin of a patient. The device has a port into which a hypodermic needle can be inserted through the skin to inject a quantity of a liquid agent, such as a medication or drug. The liquid agent is delivered from the device through a catheter port into a catheter. The catheter is positioned to deliver the agent to specific infusion sites in the sympathetic or parasympathetic nerve chain. The infusion pump may take the form of the device described in U.S. Pat. No. 4,692,147 (Duggan) or U.S. Pat. No. 6,094,598 (Elsberry et al.) which are both assigned to Medtronic, Inc., Minneapolis, Minn., and are both hereby incorporated by reference herein.

The distal end of the catheter terminates in a cylindrical hollow tube having a distal end implanted into a portion of the ganglia of interest in the sympathetic or parasympathetic nerve chain by conventional stereotactic surgical techniques. The distal end is provided with microporous portions in the preferred embodiment; however, multiple holes or slits within portions could also be used. The tube includes an outer cylindrical insulating jacket and an inner cylindrical insulating jacket that defines a cylindrical catheter lumen. A multifilar coil or strands of wire is embedded in the tube.

The tube is surgically implanted through a hole in the back of a human and the catheter is implanted at or near the ganglion of interest. A stylet may be placed into the center of the tube to give it stiffness when introducing the tube into the neural tissue. After the stylet is removed, the center lumen constitutes a catheter that can be used to infuse an agent, including a drug. The catheter is joined to the implanted infusion pump in the manner shown. The infusion pump is implanted in a human body.

Alternatively, the device may be implanted in the abdomen. The catheter may be divided into twin tubes that are implanted into the brain bilaterally as shown. Alternatively, the tube may be supplied with drugs from a separate catheter and pump. Referring again to a device made in accordance with this embodiment, the device also may be implanted below the skin of a patient. The device may take the form of a signal generator Model 7424 manufactured by Medtronic, Inc. under the trademark Itrel II which is incorporated by reference.

The distal end of the tube terminates into stimulation electrodes and each of the electrodes is individually connected to the device through a conductor in the wire. The wires exit the catheter to form a cable which is joined to the implanted device. While an embodiment may include two electrodes on the tube, some applications may require a greater number.

A drug can be delivered continuously (within the constraints of the particular delivery device being used) or it may be delivered during intermittent intervals coordinated to reflect certain time intervals such as the half-life of the particular agent being infused or circadian rhythms. As an example, symptoms may normally subside at night when the person is sleeping so the drug delivery rates might be reduced to coincide with the hours between 10 p.m. and 7 a.m.

In addition, this embodiment is extended to include a combination electrical contact and drug delivery system, as well as a system that has the capacity to sense or record electrical or chemical activity in the region of interest. A sensor may be implanted into a portion of a patient's body suitable for detecting symptoms of the physiological disorder of interest as described in U.S. Pat. No. 6,058,331 (King), assigned to Medtronic, Inc., which is hereby incorporated by reference herein. The sensor is adapted to sense an attribute of the symptom to be controlled or an important related symptom. The sensor may take the form of a device capable of detecting nerve cell or axon activity that is related to the pathways at the cause of the symptom, or that reflects sensations which are elicited by the symptom. Such a sensor may be located deep in the brain. For such detecting, sensor may take the form of an electrode inserted into the internal capsule, motor cortex, basal ganglia of the brain, spinal cord, ganglia, or nerves. Signals that are received by the sensor may by amplified before transmission to circuitry contained within devices. Yet another form of the sensor would include a device capable of detecting nerve compound action potentials (e.g., either sensory afferent information from muscle or skin receptors or efferent motor potentials controlling a muscle of interest). The sensor may take the form of a transducer consisting of an electrode with an ion selective coating applied which is capable of directly transducing the amount of a particular transmitter substance or its breakdown by-products found in the interstitial space of a region of the brain such as the ventral lateral thalamus. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in Neuroscience Letters, 120 (1990) 249–252.

In operation, the sensor generates a sensor signal related to the activity resulting from the physiological disorder. A microprocessor then regulates the stimulation in response to the sensor signal to treat the physiological disorder. The microprocessor within the device can be programmed so that a controlled amount of agent or drug can be delivered to the specific ganglia of interest. Alternatively, the sensor can be used with a closed loop feedback system to automatically determine the level of drug delivery necessary to alleviate the physiological disorder symptoms.

The output of the sensor is coupled by a cable comprising conductors to the input of analog to digital converter. Alternatively, the output of an external feedback sensor would communicate with the implanted pulse generator through a telemetry downlink. The output of the analog to digital converter is connected to terminals BAR and BAR shown in FIG. 11A of U.S. Pat. No. 4,692,147. Before converter is connected to the terminals, the demodulator currently shown in FIG. 11A would be disconnected.

Alternative approaches include posterior open extrapleural techniques, posterior percutaneous approaches, the anterior supraclavicular method, as well as the open transthoracic approach. However, while there has been described and illustrated specific embodiments of new and novel methods of treatment for physiological disorders, such as hyperhydrosis, facial blushing, complex regional pain syndromes, and abnormal cardiac sympathetic output, it will be apparent to those skilled in the art that variations and modifications are possible, such alterations shall be understood to be within the broad spirit and principle of the present invention which shall be limited solely by the scope of the claims appended hereto.

What is claimed is:

1. A method of treating heart contractility in a patient comprising:
    placing an electrode in communication with at least one ganglion along the sympathetic nerve chain of the patient, said at least one ganglion being associated with heart contractility;
    applying an electric signal to the electrode to stimulate the at least one ganglion; and
    adjusting at least one parameter of the electric signal until heart contractility has been treated.

2. The method of claim 1, wherein the at least one ganglion is selected from the group consisting of T-1 through T-4 ganglia, cervical ganglia, and combinations thereof.

3. The method of claim 1, wherein the electric signal is applied continuously.

4. The method of claim 1, wherein the electric signal is applied intermittently.

5. The method of claim 1, wherein the parameter is pulse frequency adjustable between about 2 Hz to about 2500 Hz.

6. The method of claim 1, wherein the patient has heart failure associated with cardiomyopathy.

7. The method of claim 1, wherein the patient has a heart contractility disorder.

8. The method of claim 7, wherein the heart contractility disorder is cardiomyopathy.

9. The method of claim 8, wherein the heart contractility disorder is hypertrophic cardiomyopathy.

10. The method of claim 1, wherein the parameter is pulse width adjustable between about 10 microseconds to about 1,000 microseconds.

11. The method of claim 1, wherein the parameter is pulse amplitude adjustable between about 0.1 $\mu$V to about 20 V.

12. The method of claim 1, further comprising administering an amount of a pharmaceutical agent to the at least one ganglion.

13. The method of claim 12, wherein the amount is determined based upon the effectiveness of the electrical stimulation of the at least one ganglion.

14. The method of claim 12, wherein the administration of the therapeutically effective amount of a pharmaceutical agent is accomplished by a catheter coupled to a pump.

15. The method of claim 14, wherein the catheter is placed in communication with the at least one ganglion along the sympathetic nerve chain of the patient.

16. The method of claim 1, further comprising sensing a signal related to heart contractility.

17. The method of claim 16, wherein the signal is an electrical signal.

18. The method of claim 16, wherein the signal is a chemical signal.

19. The method of claim 16, further comprising regulating the electrical stimulation in response to said signal.

* * * * *

UNITED STATES PATENT AND TRADEMARK OFFICE
CERTIFICATE OF CORRECTION

PATENT NO. : 6,885,888 B2
DATED : April 26, 2005
INVENTOR(S) : Ali Rezai

It is certified that error appears in the above-identified patent and that said Letters Patent is hereby corrected as shown below:

Column 2,
Line 52, change "beneficiary" to -- beneficial --.
Line 58, change "result to diseased" to -- result of diseased --.

Column 3,
Line 24, change "coagolaputhies" to -- coagulopathies --.
Lines 28, 30 and 44, change "coagolapathy" to -- coagulopathy --.

Column 4,
Line 56, change "anyone" to -- any one --.

Column 5,
Line 27, change "go the end organ." to -- go to the end organ. --.

Column 9,
Line 30, change "transcutanous" to -- transcutaneous --.
Line 41, change "inhibitation" to -- inhibition --.

Column 11,
Lines 10 and 18, change "effect" to -- affect --.

Column 13,
Line 28, change "effects" to -- affects --.

UNITED STATES PATENT AND TRADEMARK OFFICE
CERTIFICATE OF CORRECTION

PATENT NO. : 6,885,888 B2
DATED : April 26, 2005
INVENTOR(S) : Ali Rezai

It is certified that error appears in the above-identified patent and that said Letters Patent is hereby corrected as shown below:

Column 15,
Line 67, change "strands" to -- strand --.

Column 18,
Line 41, change "electrical" to -- electric --.

Signed and Sealed this

Thirtieth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,885,888 B2
DATED : April 26, 2005
INVENTOR(S) : Ali Rezai

It is certified that error appears in the above-identified patent and that said Letters Patent is hereby corrected as shown below:

<u>Title page,</u>
Item [63], Related U.S. Application Data, delete the whole paragraph in its entirety.

<u>Column 1,</u>
Lines 4-9, delete the whole paragraph.

<u>Column 2,</u>
Line 52, change "beneficiary" to -- beneficial --.
Line 58, change "result to diseased" to -- result of diseased --.

<u>Column 3,</u>
Line 24, change "coagolaputhies" to -- coagulopathies --.
Lines 28, 30 and 44, change "coagolapathy" to -- coagulopathy --.

<u>Column 4,</u>
Line 56, change "anyone" to -- any one --.

<u>Column 5,</u>
Line 27, change "go the end organ." to -- go to the end organ. --.

<u>Column 9,</u>
Line 30, change "transcutanous" to -- transcutaneous --.
Line 41, change "inhibitation" to -- inhibition --.

<u>Column 11,</u>
Lines 10 and 18, change "effect" to -- affect --.

<u>Column 13,</u>
Line 28, change "effects" to -- affects --.

<u>Column 15,</u>
Line 67, change "strands" to -- strand --.

UNITED STATES PATENT AND TRADEMARK OFFICE
CERTIFICATE OF CORRECTION

PATENT NO. : 6,885,888 B2
DATED : April 26, 2005
INVENTOR(S) : Ali Rezai

It is certified that error appears in the above-identified patent and that said Letters Patent is hereby corrected as shown below:

Column 18,
Line 41, change "electrical" to -- electric --.

Signed and Sealed this

Thirteenth Day of September, 2005

JON W. DUDAS
*Director of the United States Patent and Trademark Office*